United States Patent [19]

Daculsi et al.

[11] Patent Number: 5,631,016
[45] Date of Patent: May 20, 1997

[54] PROCESS FOR THE PRODUCTION OF SINGLE- OR MULTI-PHASE MATERIALS OF BIOLOGICAL INTEREST

[75] Inventors: Guy Daculsi, Vigneux de Bretagne; Catherine Deudon, Nantes, both of France

[73] Assignee: Universite De Nantes, Nantes Cedex, France

[21] Appl. No.: 428,105

[22] PCT Filed: Oct. 28, 1993

[86] PCT No.: PCT/FR93/01064

§ 371 Date: Apr. 26, 1995

§ 102(e) Date: Apr. 26, 1995

[87] PCT Pub. No.: WO94/09832

PCT Pub. Date: May 11, 1994

[30] Foreign Application Priority Data

Oct. 28, 1992 [FR] France .................... 92 12837

[51] Int. Cl.⁶ ................ A61E 2/02; A61F 2/28
[52] U.S. Cl. ............... 424/426; 523/115; 623/16
[58] Field of Search ................. 424/423, 484, 424/486, 426; 514/772.3; 623/16; 523/115

[56] References Cited

U.S. PATENT DOCUMENTS 4,218,255  8/1980  Bajpai et al. .

FOREIGN PATENT DOCUMENTS

| 0087662 | 9/1983 | European Pat. Off. . |
| 2396613 | 2/1979 | France . |
| 2138388 | 2/1973 | Germany . |
| 3706821 | 9/1988 | Germany . |

*Primary Examiner*—Carlos A. Azpuru
*Attorney, Agent, or Firm*—Young & Thompson

[57] ABSTRACT

An integrated solid body of biological interest is produced by admixing a mineral powder with a biologically active principle, and then subjecting the mixture thus obtained to a shockwave thereby to produce an integrated solid body. The shockwave is generated by explosion or by launching a projectile toward the mixture. The mixture is confined in a mold cavity prior to application of the shockwave. The mold cavity is placed under vacuum prior to application of the shockwave. Particles of the mixture are thus cold bonded to each other. The body is in the form of an implant for the human body. The mineral powder is a calcium phosphate, e.g. octocalcium phosphate, dicalcium phosphate, dihydrated dicalcium phosphate, tricalcium phosphate and tetracalcium phosphate.

7 Claims, 1 Drawing Sheet

PROCESS FOR THE PRODUCTION OF SINGLE- OR MULTI-PHASE MATERIALS OF BIOLOGICAL INTEREST

This application is a 371 of PCT/FR93/01064 filed Oct. 28, 1993.

The present invention relates to a process for the production of single- or multi-phase materials of biological interest such as composites or ceramics particularly from bioactive mineral powders such as calcium phosphate powders, as well as products for biological use obtained by practice of the process.

Mineral powders take part nowadays in the composition of a large number of products. The essential problem always resides in the interconnection of the constituents of said powders. Thus, ceramics constituted by compacted mineral powders are obtained only under the action of either high temperature and/or very high pressure, thereby giving rise to a deterioration of the structures.

Concomitantly, dynamic compaction is a process nowadays widely used as a process for bonding or connection of metallic powders. Such a process is for example described in the article of D. G. MORRIS "Bonding processes during the dynamic compaction of metallic powders", Mater. Sci. & Eng. Vol. 157, pp 187 to 195. Similarly, in the patent DE-A-2.138.388 is described a process for dynamic compaction which is applicable to compacting essentially metallic powders. The patent FR-A-2.396.613 describes a process for compacting powder by means of a shockwave generated by launching a projectile which directly strikes the matrix within the cavity of the specimens containing the powder. This patent is applicable to powders which are metallic or not, without supplemental precision.

Finally, the patent DE-A-3.706.821 discloses a process for compacting by explosion for the production of refractory ceramic members. However, in the case of all these patents, no particular application of the obtained powders is disclosed.

The principle of dynamic compaction is simple and consists in generating a shockwave also called an elastic compression wave which strikes the specimen disposed in a matrix so as to deform it while giving rise to partial fusion of the grains at their surface and hence an interconnection of the grains.

The inventors of the present invention have discovered that, in a surprising manner, it is possible to obtain with bioactive and hence biocompatible materials such as bioactive mineral powders, the same result and thus to obtain in solid form blocks of material which had never been able to be compacted with techniques currently used such as sintering. In addition to the possibility of obtaining new materials, the drawbacks connected with sintering are also avoided, which required compressing the material at high temperature so as to give rise to a fusion of the constituents, then an agglomeration of the microcrystals which form upon cooling, these latter remaining thus interconnected at the grain boundaries. This temperature elevation modifies the crystallographic properties and hence generally the biological activity of the material. Moreover, with certain mineral powders such as calcium phosphate powders, there are obtained calcium phosphate ceramics which are very fragile because the thermal exchanges in particular during the step of cooling of the sintering process give rise to stresses which tend to crack the final product.

The object of the present invention is therefore to be able to provide, particularly from bioactive mineral powders, ceramics, indeed composites, by association with metallic or non-metallic matrices, without temperature elevation and with the possibilities of controlling the size and shape of the final crystals as well as the homogeneity of the mixture obtained, while maintaining optimum biological activity of the composition.

Another object of the present invention is to be able to associate organic substances, particularly the active principles, without degradation of these latter, with these mineral powders to obtain a progressive diffusion of said principle within the organism.

Finally, a last object of the invention is to obtain new ceramics based particularly on calcium salts in particular calcium phosphates never before produced.

The invention thus concerns a process for the production of materials, for biological use, which are single- or multi-phase such as composites or ceramics particularly from mineral powders, characterized in that a specimen containing at least said bioactive mineral powder is dynamically compacted by means of a shockwave.

The invention also relates to all single- or multi-phase biocompatible products such as ceramics or composites based among other things on bioactive mineral powder such as a powder of calcium salts, particularly of calcium phosphates whose grains are cold bonded to each other.

Other characteristics and advantages of the invention will become apparent from a reading of the description which follows and the accompanying drawings, which description and drawings are given only by way of example. In these drawings.

The process according to the invention permits providing bioactive products and hence biocompatible products particularly from bioactive mineral powders, preferably powders of calcium phosphate. The products obtained are constituted by ceramic-based products associated or not with other elements such as metal or resin or polymers, etc., accordingly as it is desired to provide a ceramic of pure mineral powder or a composite mineral. These products are destined for example for the production of osseous or cartilaginous implants, for the provision of biodegradable filling products, etc.

To obtain such a result, it is necessary to introduce a specimen comprising particularly a bioactive mineral powder, that is to say a mineral powder whose constituents have a biological activity which can consist in a modification of the cellular activity, in a healing activity, in an expression of the phenotype of the cell, etc. by shifting of the ion exchanges between said constituent elements. The constituent mineral elements can be any whatsoever. However, it is preferable that at least one of the elements of this powder be chosen from the group of calcium salts, in particular calcium phosphates comprising octocalcium phosphates, dicalcium phosphates, hydrated dicalcium phosphates, tricalcium phosphates and tetracalcium phosphates. In a second step, there is generated a shockwave also called an elastic compression which deforms the specimen and hence densifies it so as to compact it. The shockwave which deforms the specimen and permits its compacting can be generated in various manners.

Figure 1:
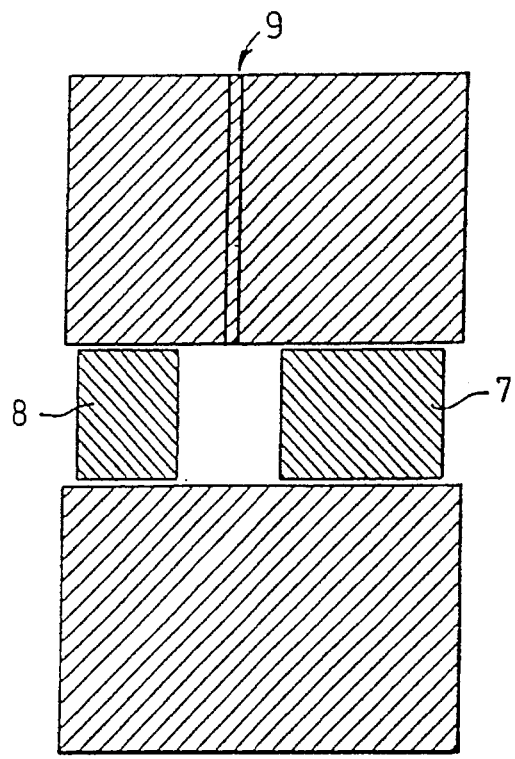
FIG. 1 shows a cross-sectional view of a compacting matrix.
Figure 2:
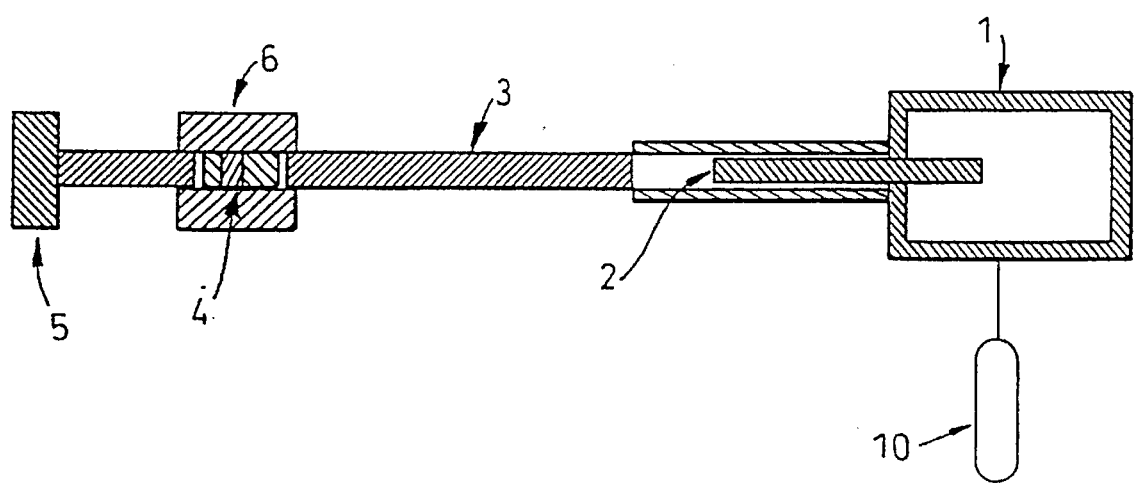
FIG. 2 shows a simplified schematic view of a device permitting dynamic compacting of powders.

An example of a device permitting the practice of this process is shown in FIG. 2. This device comprises means for generating a shockwave which are here constituted by a gas launcher designated by 1, associated with a projectile. The projectile designated by 2 is propelled by the pressure of the launcher and strikes the incidence bar 3 thereby creating an elastic compression wave. This bar strikes the specimen 4 disposed in the matrix 6 thereby creating a deformation and hence a densification of the powders to be compacted. When the wave reaches the specimen, a portion is reflected into the incidence bar 3 and the other portion is transmitted to the specimen. The shock absorption is ensured by a shock absorber constituted by a transmission bar 5. We will speak in the example shown in FIG. 1 of an indirect compacting to the extent that the shock is imposed on the incidence bar 3 and is transmitted by said bar 3 to the specimen.

It could also be arranged that the shock is directly transmitted to the specimen, the projectile coming directly into contact with the specimen or the walls of the matrix. It could also be arranged, in another embodiment of the invention, to replace the gas launcher and the projectile by an explosive which gives rise to the generation of a shockwave acting either directly on the walls of the matrix and/or of the specimen, or indirectly via various transmission means for the wave. It is in that case also a matter of direct or indirect compacting.

The speed of propulsion of the projectile can vary as a function of the composition of the powders. It is generally of the order of 60 m/s with a cannon charged under a pressure of 15 bars. The Hopkinson bars used, namely the incidence bar 3 and the transmission bar 5, are steel bars which are highly resistant to the compression transmitted during shock by the projectile. The matrix 6 utilized to contain the specimen is generally comprised of a cylinder open at its two ends. This matrix constitutes obviously the compacting chamber and can constitute moreover a mold cavity. In this case, the products obtained do not need to be machined after compacting. On the contrary, the interior of this matrix can be made of a block of material, the block being then machined to obtain the desired shape.

The powders to be compacted are generally retained within the matrix by two plugs closing the ends of the cylinder, as shown in FIG. 1 in which the powder to be compacted is disposed between a compacting pallet 7 and a counter-pallet 8. To avoid the formation of an air cushion which is undesirable for compacting and to avoid any contamination of the powders, the chamber containing the powders is placed under secondary vacuum; the vacuum is of the order of $3\times10^2$ Pa. The vacuum pumping system is connected to a pumping channel 9 of vacuum of the cylindrical chamber of the powders. To effect sealing at the pump intake from the interior, aluminum membranes are disposed between the bars and the plugs, fixed to the ends of the cylinder.

Obviously, so that the incidence bar and the transmission bar will completely fulfill their role, there are provided guide rings which assure the centering of said bars. According to the materials utilized and the mixtures in question, the pressures vary. There have been used for example pressures of the order of 15 bars to compact calcium phosphate based powders of different formulations. On the contrary, strokes have been effected at 40 bars to compact metal/calcium phosphate composites. Similarly, these pressures have been used to compact calcium phosphate base ceramics having crystals of large specific area impossible to produce by conventional methods.

Thanks to the practice of this process, there are obtained calcium phosphate ceramics or composite products which permit obtaining an improved osteo-integration, particularly when they constitute implants, by reason of the fact that the process permits better controlling the physico-chemical properties such as the temperature of preparation of said ceramics which acts on the porosity and on the size of the crystals of the obtained material. Moreover, it is possible to provide the association of such a mineral powder base product, in particular calcium phosphate powder, with an active principle which can be a growth factor, an antibiotic, etc., or with any other active organic substance. This product can be integrated in powder or liquid form before compacting because the process does not include a rise in temperature. There is thus obtained particularly when using the product with a mineral powder base as an implant, the possibility of progressive diffusion of the active principle.

Similarly, it is possible, thanks to this process, to obtain new products which may be composite products or simple ceramics, from elements selected from the group comprising octocalcium phosphates, dicalcium phosphates, dihydrated dicalcium phosphates, etc. . . . There are thus obtained new biomaterials whose properties are particularly interesting. Thus, the process permits maintaining in the course of the compaction the size and shape of the original crystals. As a result, these materials resembling ceramics are perfectly identifiable with a scanning electronic microscope and with transmission microscopy because of the size and the shape of the crystals obtained. Thus, elongated crystals are always obtained at low temperature. At high temperature, generally, the crystals are present in the form of small spheres. It is thus quite easy to identify whether a ceramic obtained has or has not required the practice of the process.

The invention is not limited to biocompatible materials which are calcium phosphate based, but includes on the contrary all materials obtained by dynamic compacting of a powder containing particularly a bioactive mineral, with or without active principle, whether this latter be an adhesive agent, a chemotachism agent, an antibiotic, an antimitotic, a hormone or a growth factor.

We claim:

1. Process for producing a solid block of material of biological interest, consisting essentially of forming a specimen by integrating into calcium phosphate powder a biologically active principle in powder or liquid form, confining the specimen thus obtained in a mold cavity, and then subjecting the specimen in the mold cavity to a shockwave thereby to produce said solid block by cold bonding the particles of said calcium phosphate powder to each other.

2. A process as claimed in claim 1, wherein said shockwave is generated by explosion.

3. A process as claimed in claim 1, wherein said shockwave is generated by launching a projectile toward said mixture.

4. A process according to claim 1, and placing said mold cavity under vacuum prior to application of said shockwave.

5. A solid block of material of biological interest, consisting essentially of calcium phosphate powder which has been integrated into said solid block by application thereto of a shockwave, and a biologically active principle which as been integrated into said calcium phosphate powder in powder or liquid form prior to application of said shockwave, the particles of said calcium phosphate powder being cold bonded to each other by said shockwave.

6. A solid block of material of biological interest, as claimed in claim 5, in the form of an implant for the human body.

7. A solid block of material of biological interest, as claimed in claim 5, wherein said calcium phosphate is selected from the group consisting of octocalcium phosphate, dicalcium phosphate, dihydrated dicalcium phosphate, tricalcium phosphate and tetracalcium phosphate.

* * * * *